United States Patent [19]

Padovani et al.

[11] Patent Number: 5,792,337
[45] Date of Patent: Aug. 11, 1998

[54] METHOD AND APPARATUS FOR DETECTION OF CORROSION

[75] Inventors: Francois A. Padovani, Westwood; Paul P. Danesi, Jr., Attleboro; John F. Paster, Norfolk, all of Mass.

[73] Assignee: Texas Instruments Incorporated, Dallas, Tex.

[21] Appl. No.: 526,124

[22] Filed: Sep. 8, 1995

Related U.S. Application Data

[63] Continuation of Ser. No. 241,819, May 12, 1994, abandoned.
[51] Int. Cl.⁶ ................................................. G01N 27/26
[52] U.S. Cl. ........................... 205/775.5; 205/776.5; 205/777; 324/700; 342/42; 342/44; 342/50; 342/51
[58] Field of Search ............................ 204/404, 406, 204/400, 153.11, 153.1; 324/700, 71.2; 342/42, 44, 50, 51

[56] References Cited

U.S. PATENT DOCUMENTS

| | | | |
|---|---|---|---|
| 4,147,596 | 4/1979 | Baboian et al. | 204/404 |
| 4,333,072 | 6/1982 | Beigel | 340/825 |
| 4,958,130 | 9/1990 | Mochizuki et al. | 204/153.11 |
| 5,041,826 | 8/1991 | Milheiser | 340/825 |
| 5,053,774 | 10/1991 | Schuermann et al. | 342/44 |

*Primary Examiner*—Bruce F. Bell
*Attorney, Agent, or Firm*—Rebecca Mapstone-Lake; James C. Kesterson; Richard L. Donaldson

[57] ABSTRACT

A method and apparatus for sensing corrosion are provided in which an interrogation unit (14) transmits interrogation pulses and receives responses. A plurality of corrosion sensors (12) are disposed in the structure to be monitored (10), each of the sensors (12) generating an output. A plurality of responders (16) are powered from the interrogation pulses, one each of the responders (16) associated with one each of the sensors (12). The responders (16) are operable to transmit responses to the interrogation pulses based on the corrosion sensors' (12) output.

21 Claims, 3 Drawing Sheets

METHOD AND APPARATUS FOR DETECTION OF CORROSION

This application is a Continuation of application Ser. No. 08/241,819 filed May 12, 1994 now abandoned.

TECHNICAL FIELD OF THE INVENTION

This invention relates generally to electronic devices, and more particularly to a method and apparatus for detecting corrosion.

BACKGROUND OF THE INVENTION

Corrosion is a well-known culprit in the weakening of structural components. For example, in works such as bridges, dams, buildings, and retention walls, corrosion causes structural weakening and can lead to ultimate structural failure. Such failures are extremely dangerous, and require expensive repair.

A typical source of corrosion in structural components is metal supports. Metal supports may be in the form of rebar (used to reinforce concrete), metal beams, or other metal support members. When exposed to moisture, these metal support members corrode. This corrosion results in weakening, not only of the metal supports, but also of other support structures, such as concrete. For example, with iron support members, corrosion in the form of rust weakens the metal support members, and leaches into concrete causing deterioration and weakening of the concrete.

One cause of corrosion is the cracking of concrete, which, for example, allows moisture to reach rebar. It is possible, therefore, to prevent some corrosion by sealing such cracks. In other instances, the effects of corrosion can be remedied only by replacing the corroded members.

With an aging infrastructure such as that of the United States, it is important to ensure that the effects of corrosion are remedied before dangerous conditions arise. Corrosion damage can be minimized in both old and new structures by monitoring corrosion, and making repairs to prevent significant deterioration.

SUMMARY OF THE INVENTION

Therefore, a need has arisen for a method and apparatus for detecting corrosion which will allow repair of structures before expensive repairs are needed and before dangerous conditions arise.

Furthermore, a need has arisen for an apparatus for detecting corrosion that is small and inexpensive, and which may be conveniently monitored.

In accordance with the teachings of the present invention, a method and apparatus for detecting corrosion are presented which would substantially eliminate or reduce disadvantages and problems associated with prior art systems.

In particular, a corrosion sensing system for monitoring a structure is provided with an interrogation unit operable to transmit interrogation pulses and to receive responses. A plurality of corrosion sensors are disposed in the structure to be monitored, with each of the sensors generating an output. Also, a plurality of responders that are powered from the interrogation pulses are associated with each of the sensors. The responders are operable to transmit responses to the interrogation pulses based on the corrosion sensors' outputs.

A particular application for the corrosion sensing system is that for sensing corrosion on bridges. In a particular application of a bridge corrosion sensing system, each of a plurality of responders has an address. Furthermore, an interrogation unit is operable to transmit interrogation pulses, with at least some of the interrogation pulses including individual addresses. Each of the responders has a demodulator for demodulating the interrogation pulses into addresses, and a processor for comparing the demodulated address with the responder address. Enabling circuitry is provided in the responders for responding to the interrogation pulses only when the demodulated address matches the responder address. Furthermore, the interrogation unit may be transported in a vehicle, such that the interrogation pulses and responses are transmitted and received when the vehicle passes in proximity with the bridge.

Furthermore, a method of sensing corrosion of a structure is provided which includes transmitting interrogation pulses from an interrogation unit to a plurality of responders, with each of the responders associated with a corrosion sensor disposed in the structure to be monitored. Interrogation pulses are received at the responders, and responders are powered from the interrogation pulses. Corrosion sensing is performed and responses are transmitted to the interrogation pulses based on information from the corrosion sensing.

An important technical advantage of the present invention is the fact that remote corrosion monitoring can be performed conveniently and inexpensively. In particular, the corrosion sensors are associated with responders that do not require a local battery or other power supply. Instead, the responders are powered from interrogation pulses received from the interrogation unit. Furthermore, the corrosion sensors are relatively small, and inexpensive.

BRIEF DESCRIPTION OF THE DRAWINGS

For a more complete understanding of the present invention and the advantages thereof, reference is now made to the following description taken in conjunction with the accompanying drawings in which like reference numbers indicate like features and wherein.

DETAILED DESCRIPTION OF THE INVENTION

Figure 1:
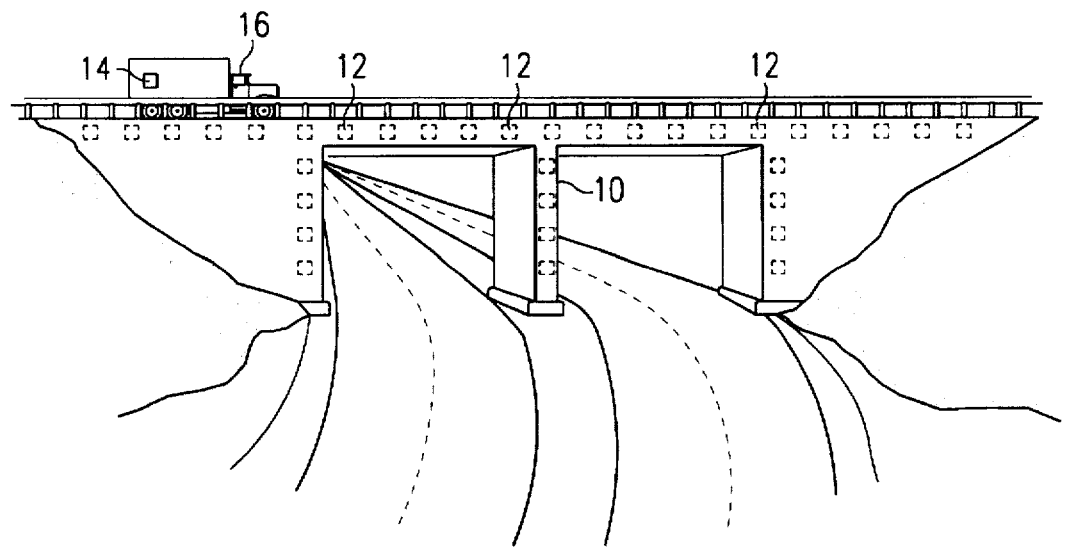
FIG. 1 illustrates a bridge with a plurality of corrosion sensors according to the teachings of the present invention.

FIG. 1 illustrates a bridge 10 including a plurality of corrosion sensors 12. Exemplary positions of the corrosion sensors 12 are indicated in FIG. 1, and the sensors 12 are placed throughout the structural elements of the bridge 10. It should be understood that a bridge is used for example only, and other structures, such as buildings, retaining walls, and dams are also to be monitored according to the present invention. The locations of the sensors 12 will depend on the particular structure being monitored, but sensors should be placed in at least those locations where corrosion damage is likely to cause the most damage.

As will be discussed below, information from the corrosion sensors 12 will be transmitted after an interrogation. The interrogation is performed with an interrogation unit 14 carried on a vehicle 15. The interrogation unit 14 records data from the corrosion sensors as the vehicle 15 passes in proximity to the sensors 12. It should be understood that the interrogation unit 14 need not be carried on the vehicle 15, and may be hand held or permanently mounted near the structure to be monitored. With structures such as bridges, however, mounting the interrogation unit 14 on a vehicle allows for particularly convenient monitoring of corrosion.

Figure 2:
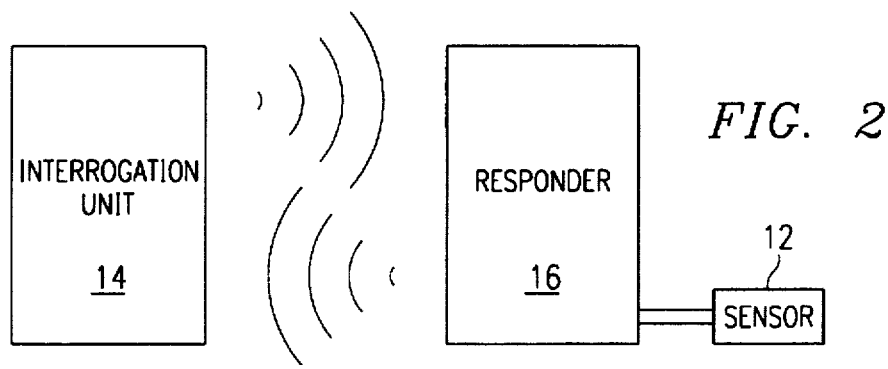
FIG. 2 is a block diagram illustrating communications between an interrogation unit and a responder and sensor according to the teachings of the present invention.

FIG. 2 illustrates communications between corrosion sensors 12 and interrogation unit 14. In particular, each corrosion sensor 12 is coupled to a responder 16. The responder 16 is able to communicate with interrogation unit 14 through the use of radio frequency ("RF") waves. With this approach, wireless, contactless reading of the corrosion sensors 12 may be accomplished. Such communication provides an important technical advantage of the present invention, since reading of the sensors 12 may be performed conveniently and quickly.

Figure 3:
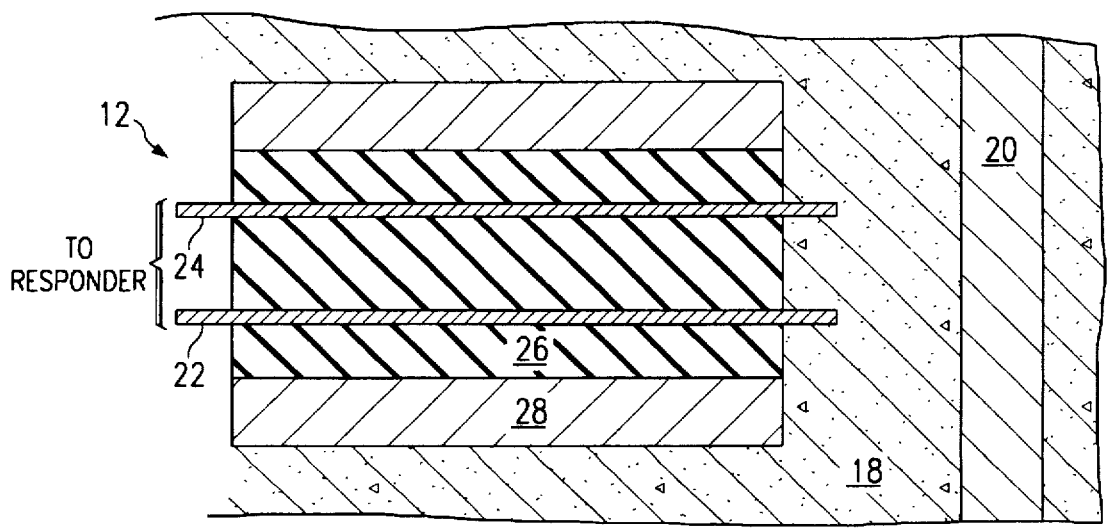
FIG. 3 illustrates a diagram of a corrosion sensor embedded in concrete according to the teachings of the present invention.

FIG. 3 illustrates a particular embodiment of a corrosion sensor 12. As shown in the example of FIG. 3, the corrosion sensor 12 is embedded in concrete 18. The corrosion sensor 12 is placed in proximity with, for example within a few centimeters, a metal support 20, which may be iron rebar, for example. Corrosion sensor 12 includes electrode wires 22 and 24. Electrode wires 22 and 24 are maintained in a spaced relation to each other by potting material 26. Potting material 26 is any conventional electrically insulative material, and should be nonreactive to any corrosives that may contact it, such as those generated when metal support 20 is exposed to moisture.

An envelope layer 28 is provided for housing the corrosion sensor 12. Envelope layer 28 may be a layer of material such as glass or plastic.

It should be understood that the particular corrosion sensor illustrated in FIG. 3 is exemplary only, and other corrosion sensors may also be used without departing from the intended scope of the present invention. Furthermore, the electrodes shown in FIG. 3 are in wire form, but it should be understood that other electrode configurations may also be used. Furthermore, the electrode 24 may be a single electrode, a clad metal electrode, or a dual electrode, among other configurations.

The electrode 22 serves as a reference electrode, and may be any standard commercial reference electrode, made out of the material from the calomel family, the silver family (including Ag/Ag halide and Ag/AgO), the copper family (including Cu/Cu halide and Cu/CuSo$_4$), or other stable reference electrode materials. The electrode 24 is a sensor electrode, and may be composed of materials such as carbon steel, copper, nickel, zinc, titanium, columbium, platinum, gold, lead, tin, or other suitable metals. The sensor electrode 24 should be of the same metal as that used in the structure being monitored.

In operation, different potentials will exist on the electrodes 22 and 24, and these potentials will change depending on whether a corrosive environment is present. By monitoring the potential difference between the electrodes, a determination can be made as to whether corrosion is present. For example, if metal support 20 began to corrode, so would sensor electrode 24, and the potential difference between the electrodes 22 and 24 would change, and this change can be registered and analyzed.

U.S. Pat. No. 4,147,596, entitled "Method and Apparatus for Monitoring the Effectiveness of Corrosion Inhibition of Coolant Fluid," issued on Apr. 3, 1979, describes particular corrosion sensors, and is herein incorporated by reference. Corrosion sensor 12 of the present invention may be constructed in accordance with the teachings of that patent. Furthermore, other corrosion sensors may be used without departing from the intended scope of the present invention. For example, varying corrosion scenarios will be presented depending upon the nature of the materials in the structure to be monitored, and corrosion sensors with electrodes formed of different materials, and other types of corrosion sensors altogether, may be appropriate.

Figure 4:
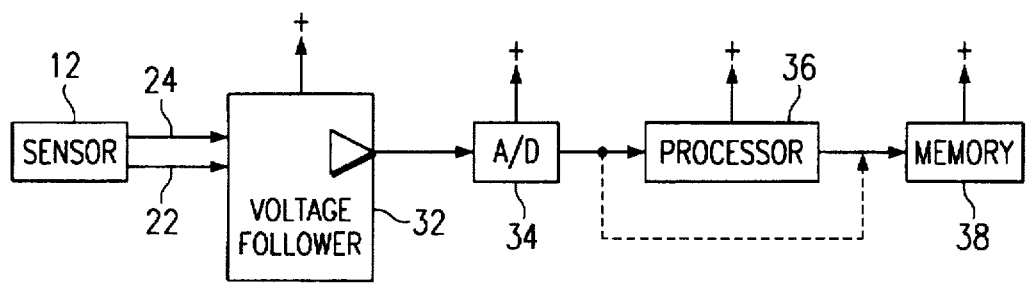
FIG. 4 illustrates a block diagram of an embodiment of circuitry for reading a corrosion sensor according to the teachings of the present invention.

FIG. 4 illustrates a block diagram of circuitry for reading the sensor 12. As shown in FIG. 4, electrodes 24 and 22 from sensor 12 are input to a voltage follower 32. Voltage follower 32 outputs a signal proportional to the potential difference between electrodes 22 and 24. This output may be amplified. The output of voltage follower 32 is input to analog to digital converter 34, which converts the signal to a digital signal. This digital signal is then read by a processor 36 and stored in memory 38. Processor 36 may direct the output of analog to digital converter 34 directly to memory 38, as shown by the dashed line of FIG. 4.

As will be discussed below, an important technical advantage of the present invention is the fact that the sensor reading circuitry may be powered by an interrogation pulse sent by interrogation unit 14. Thus, the sensor 12 and reading circuitry does not need a battery or other local power source. Because no battery is needed, the sensor 12 and associated circuitry may be placed in the structure to be monitored and thereafter little or no maintenance is required on the sensor.

Figure 5:
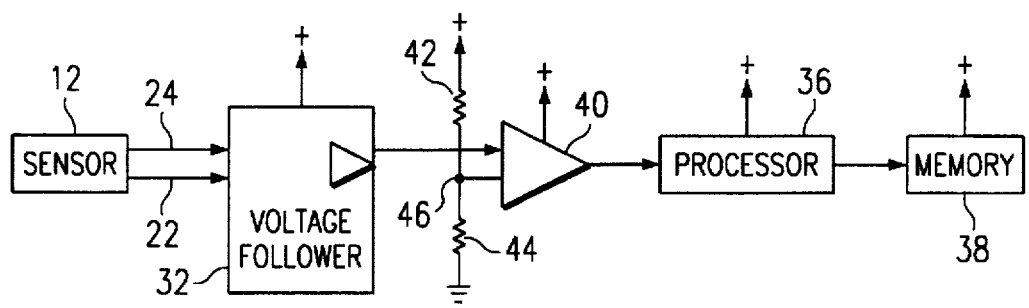
FIG. 5 is another embodiment of circuitry for reading a corrosion sensor according to the teachings of the present invention.

FIG. 5 illustrates another embodiment of circuitry for reading the sensor 12 according to the teachings of the present invention. As shown in FIG. 5, voltage follower 32 outputs a signal that is proportional to the potential difference existing between the electrodes 22 and 24 of sensor 12. The output of voltage follower 32 is coupled to the input of a comparator 40. Comparator 40 compares the output of voltage follower 32 with a reference voltage at node 46 generated by resistor dividers 42 and 44. Thus, the output of comparator 40 will be in one state if the output of voltage follower 32 is less than the voltage at node 46, and the output of comparator 40 will be in another state if the output of voltage follower 32 is greater than the voltage at node 46.

The voltage at node 46 may be set by analyzing what level of corrosion is acceptable. For example, the voltage level at node 46 may be set such that the state of comparator 40 changes when the output of the sensor 12, and thus the corrosion, reaches a certain set point. This set point may correspond to the condition at which enough corrosion has occurred to require maintenance, but not so much corrosion as to indicate a dangerous condition. Processor 36 reads the output of comparator 40 and then stores information based on that output in memory 38.

The two embodiments shown in FIG. 4 and FIG. 5 for circuitry for reading the sensors 12 are exemplary only. It should be understood that other circuits may be used to read and record information from sensors 12 without departing from the intended scope of the present invention.

Figure 6:
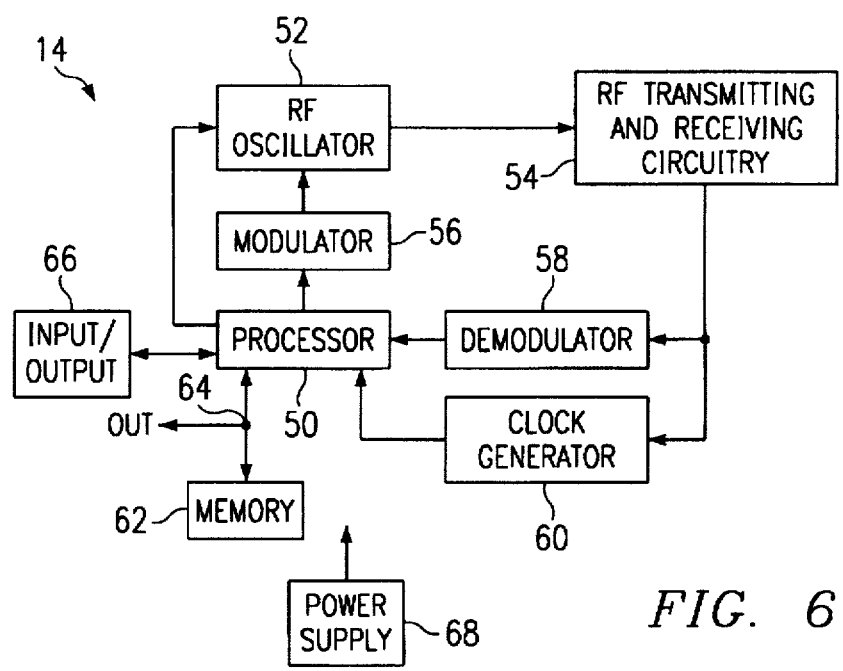
FIG. 6 is a block diagram of an interrogation unit according to the teachings of the present invention.

FIG. 6 illustrates a block diagram of interrogation unit 14 according to the teachings of the present invention. As shown in FIG. 14, a processor 50 controls RF oscillator 52. RF oscillator 52 generates an output that is coupled to RF transmitting and receiving circuitry 54. In a particular example, RF oscillator may operate at a nominal frequency of 125 kHz. Processor 50 is also coupled to a modulator 56 which may be used to modulate the frequency (or amplitude or phase) of the output of RF oscillator 52. RF transmitting and receiving circuitry 54 is also coupled to demodulator 58 and clock generator 60. Demodulator 58 and clock generator 60 are coupled to processor 50. Processor 50 stores information received from demodulator 58 into memory 62.

Data from memory 62 or processor 50 may also be output to an external system, such as a storage and analysis system through output 64. Similarly, data can be output to input/output device 66 as shown in FIG. 6. Input/output device 66 may also be used to initiate operation of interrogation unit 14. Input/output device 66 also may comprise a display, on which information received from corrosion sensors 12 may be displayed. A power supply 68 is provided for powering interrogation unit 14. Power supply 68 may be a rechargeable battery, nonrechargeable battery, or other power supply.

In operation, interrogation unit 14 will be activated to read information from corrosion sensors 12. As shown in FIG. 1, for example, as a vehicle carrying interrogation unit 14 passes over the bridge 10, the interrogation operation may be initiated.

RF transmitting and receiving circuitry 54 transmits an interrogation pulse, and sometime thereafter, a response is received. This response is input to clock generator 60 and demodulator 58. Clock generator 60 generates a clock based on the returned signal, and demodulator circuit 58 demodulates the response. For example, the response may have been modulated using frequency-shift keying ("FSK"). Thus, a response at a particular frequency for a given amount of time will be recognized as a "0" and a received signal at another frequency received for a given amount of time will be recognized as a "1". Processor 50 will read these "1s" and "0s" and store them in memory 62 and may also present them for output at output 64 or to input/output device 66.

It may be desirable to individually address each of the corrosion sensors 12 being used to monitor a particular structure. With individual addressing, the locations of particular sensors are maintained in a record, and data from those sensors then correlated with their position. Modulator 56 is provided for this purpose. In particular, the frequency (or amplitude or phase) of the output of RF oscillator 52 is modulated by modulator 56, which is controlled by processor 50. In this way, an interrogation pulse generated by RF transmitting and receiving circuitry 54 will be modulated according to a particular address of the particular corrosion sensor 12 to be read. Thus, only that corrosion sensor 12 will respond to the particularly addressed interrogation pulse. Processor 50 will then record the received data as corresponding to that particularly addressed corrosion sensor 12.

A particular embodiment of interrogation unit 14 is described in U.S. Pat. No. 5,053,774 entitled "Transponder Arrangement" and issued on Oct. 1, 1991. That patent is herein incorporated by reference.

Figures 7, 8:
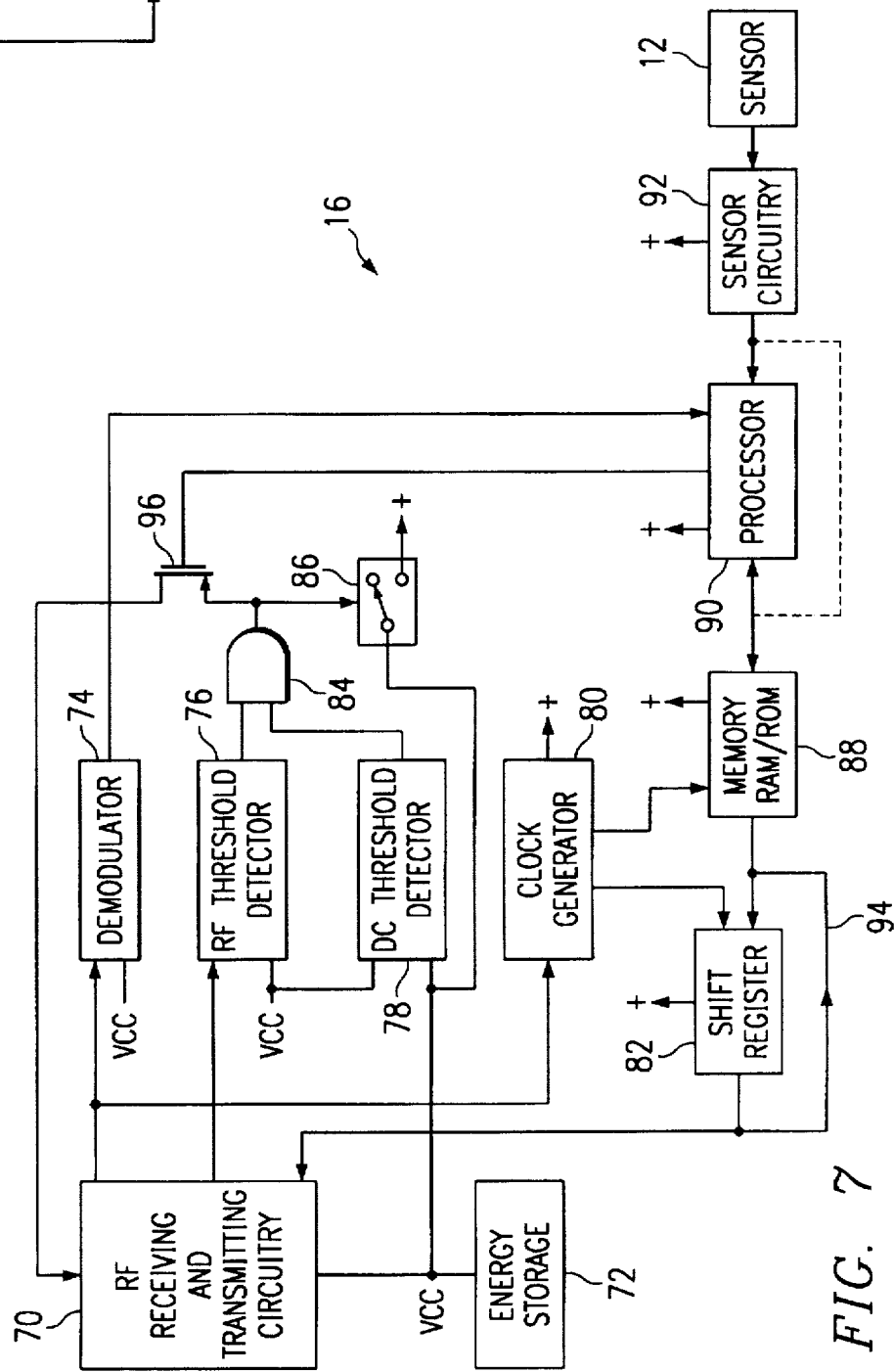
FIG. 7 is a block diagram of a responder unit according to the teachings of the present invention.
FIG. 8 is a block diagram of a system for storing and analyzing data generated according to the teachings of the present invention.

FIG. 7 illustrates a block diagram of a responder 16 according to the teachings of the present invention. As shown in FIG. 7, RF receiving and transmitting circuitry 70 is coupled to an energy storage 72, demodulator 74, RF threshold detector 76, DC threshold detector 78, clock generator 80, and shift register 82. RF threshold detector 76 and DC threshold detector 78 are coupled to circuitry 84 which provides an output signal only if there is an input signal from both RF threshold detector 76 and DC threshold detector 78. Such a circuit is typically referred to as an "AND" gate. Therefore, the output of AND gate 84 controls a switch 86 which is used to couple power from energy storage 72 to clock generator 80 and shift register 82. The output of AND gate 84 is also coupled to circuitry 70 (as shown, through a switch 96 to be discussed, which is included for individual addressing). Also, the output of switch 86 is coupled to a memory 88, a processor 90, and sensor circuitry 92. The memory 88 is coupled to processor 90, clock generator 80, and shift register 82. The processor 90 is also coupled to demodulator 74 and sensor circuitry 92. Sensor circuitry 92, as described above in connection with FIG. 4 and FIG. 5, is used to read the output of corrosion sensor 12 for processing and storage.

In operation, RF receiving and transmitting circuitry 70 receives an interrogation pulse from interrogation unit 14. As the pulse is received, energy is stored in energy storage 72, which may comprise a capacitor. At the end of the interrogation pulse, RF threshold detector 76 will detect the decreased received RF energy, and will output a signal to AND gate 84. As discussed above, the received energy from the RF interrogation pulse is stored in energy storage 72. Energy storage 72 will be used to power all of the circuitry within responder 16. Thus, no local battery or other power supply is needed for responder 16. This provides an important technical advantage, since the responder 16 will thus not need any maintenance.

Once the energy level within energy storage 72 reaches a level sufficient to power each of the devices within responder 16, DC threshold detector 78 will also output a signal to AND gate 84. Once the outputs from both detector 76 and 78 are received by AND gate 84, switch 86 will be activated, thus powering up the other circuitry on the responder 16.

The output of AND gate 84 is also coupled to circuitry 70 and triggers the transfer of energy from energy storage 72 through circuitry 70 to generate an RF carrier signal to be transmitted back to interrogation unit 14. This RF carrier signal is also used to generate clock signals through clock generator 80. Clock generator 80 controls shift register 82 and memory 88 such that data stored in memory 88 is transferred to shift register 82. The data output from shift register 82 is transmitted to RF receiving and transmitting circuitry 70. This output is used to modulate the RF carrier wave output by circuitry 70. For example, the bits output by shift register 82 may be used to cause FSK modulation of the RF carrier wave output by circuitry 70. Shift register 82 may also include a feedback loop 94. Feedback loop 94 will be used once all data to be transmitted are loaded within shift register 82. These bits will then be reloaded into the shift register as they are shifted out, so that the data to be transmitted to interrogation unit 14 may be retransmitted again and again without need to reaccess memory 88.

As discussed above, the sensor circuitry 92 reads the output of sensor 12. Processor 90 loads the output of sensor circuitry 92 into memory 88, or loads information into memory 88 based on the output of sensor circuitry 92. Memory 88 may be a combination of random access memory and read only memory. The particular address of sensor 12 read by responder 16 may be included in the ROM portion of memory 88. The RAM portion of memory 88 will store the particular data generated by sensor circuitry 92 and processor 90. Such address and sensor data will then be loaded from memory 88 to shift register 82.

The demodulator circuit 74 demodulates signals from interrogation unit 14. The output of demodulator 74 is input to processor 90. Processor 90 compares the information demodulated by demodulator 74 with address data stored in memory 88. If the demodulated data from demodulator 74 corresponds to the data stored in memory 88, then the particular responder 16 and sensor 12 has been addressed, and should respond. If the data does not match, then the particular responder has not been addressed, and will not respond.

Individual addressing may be accomplished by transmitting a wake-up pulse from the interrogation unit 14 followed by an address pulse, which contains the address of the responder/sensor to be addressed. The wake-up pulse provides energy for powering the processor 90 and demodulator 74, which then analyze the address pulse to determine whether the particular responder 16 has been addressed. Energy from the address pulse can also be used to power the responder. Furthermore, the wake-up and address pulse may be a single pulse. The demodulator 74 as shown is powered directly from energy storage 72. Demodulator 74 may be powered through switch 86. For example, with one combined wake-up and interrogation pulse, demodulator 74 should be powered directly from energy storage 72. With two separate pulses, demodulator 74 may be powered through switch 86, since power would be received before the interrogation pulse arrived. It should be understood that demodulator 74 need not be included, and no addressing is required. In such an instance, each responder within the range of the interrogation pulse responds to interrogation unit 14.

With individual addressing, the output of AND gate 84 that is coupled to RF receiving and transmitting circuitry 70 will be passed through a switch 96. Switch 96 is controlled by processor 90. Switch 96 will be closed only if the address received from interrogation unit 14 corresponds to the address of the responder 16. With the switch 96 open, no response is enabled. Thus the switch and its control are enabling circuitry.

The processor 90 may be a microprocessor, microcontroller, programmable array logic, gate array logic, or any other circuitry capable of performing the logic and control functions discussed herein.

A particular embodiment for responder unit 16 is disclosed in U.S. Pat. No. 5,053,774, entitled "Transponder Arrangement," and issued on Oct. 1, 1991. That patent is herein incorporated by reference.

FIG. 8 illustrates a particular embodiment of a system for storing and analyzing data received from responders 16. As shown in FIG. 8, interrogation unit 14 is coupled to storage/analysis system 98. Storage/analysis system 98 is operable to analyze information stored in interrogation unit 14 received from the particular responder 16. Thus, the storage/analysis system 98 is able to correlate corrosion information from the responders 16 with information on the location of the particular responders, and present information as to the state of corrosion of the particular structure being monitored. The link between interrogation unit 14 and storage/analysis system 98 may be a direct wire link, or a contactless link such as may be provided through induction coils or infrared transmission.

In summary, a method and apparatus for detecting corrosion has been described in which convenient and inexpensive gathering of data from particular corrosion sensors is accomplished. Furthermore, the particular corrosion sensors described are self contained, and do not require a local power supply, and thus are nearly maintenance-free.

Although the present invention has been described in detail, it should be understood that various changes, substitutions, and alterations can be made without departing from the intended scope as defined by the appended claims.

What is claimed is:

1. A corrosion sensing system for monitoring a structure at least partially constructed with metal, comprising:
   an interrogation unit to transmit interrogation pulses and to receive responses;
   a plurality of corrosion sensors disposed in proximity to said metal in said structure to be monitored, each of said sensors powered by said interrogation pulse and generating an output representative of the occurrence of corrosion; and
   a plurality of responders powered by said interrogation pulses, one each of said responders associated with one each of said sensors, said responders transmitting responses to said interrogation pulses based on said corrosion sensors' outputs.

2. The system of claim 1, wherein each of said corrosion sensors comprises:
   a reference electrode; and
   a sensor electrode, affected by corrosion in a manner similar to corrosion affecting said metal in said structure such that the potential difference between said electrodes is indicative of corrosion.

3. The system of claim 2 wherein said sensor electrode is made of the same metal used in constructing said structure.

4. The system of claim 3 wherein said structure is made of concrete and metal reinforcement members.

5. The system of claim 1, and further comprising a vehicle, said interrogation unit transported in said vehicle such that said interrogation pulses and said responses are transmitted and received as said vehicle passes in proximity with the structure to be monitored.

6. The system of claim 1, wherein each of said responders further comprises read circuitry generating data based on said output from an associated corrosion sensor.

7. The system of claim 6, wherein said read circuitry comprises:
   a voltage follower coupled to said corrosion sensor;
   an analog to digital converter coupled to said voltage follower;
   a processor coupled to said analog to digital converter; and
   a memory coupled to said processor, such that said processor directs data from said analog to digital converter to said memory.

8. The system of claim 6, wherein said read circuitry comprises:
   a voltage follower coupled to said corrosion sensor, said voltage follower generating a voltage based on said corrosion sensor output;
   a comparator coupled to said voltage follower, said comparator having a first output state and a second output state, depending on the level of said corrosion sensor output;
   a processor coupled to said comparator; and
   a memory coupled to said processor, said processor operable to store information related to the state of said comparator to said memory.

9. The system of claim 1, wherein said interrogation unit modulates at least some of said interrogation pulses to provide individual responder addressing, and wherein each of said responders comprises:

a demodulator to demodulate interrogation pulses into addresses;

a processor coupled to said demodulator to compare the demodulated addresses with a responder address; and a switch to enable responses only when said demodulated addresses match said responder address.

10. The system of claim 1, wherein said interrogation pulses comprise wake-up pulses and address pulses, and wherein each of said responders comprises:

energy storage for storing energy from said wake-up pulses and said address pulses;

a demodulator coupled to said energy storage to demodulate interrogation pulses into addresses;

a processor coupled to said demodulator the demodulated addresses with a responder address; and a switch to enable responses only when said demodulated addresses match said responder address.

11. A corrosion sensing system for monitoring a structure constructed from concrete and metal reinforcement members, comprising:

an interrogation unit to transmit interrogation pulses and to receive responses, at least some of said interrogation pulses including individual addresses;

a plurality of corrosion sensors disposed in the concrete structure to be monitored and in proximity with said metal reinforcing members, each of said sensors generating an output representative of corrosion;

a plurality of responders each having an address and each powered by said interrogation pulses, one each of said responders associated with one each of said sensors, said responders operable to transmit responses to said interrogation pulses based on said corrosion sensors' outputs, each of said responders including:

a demodulator to demodulate interrogation pulses into addresses;

a processor coupled to said demodulator and operable to compare the demodulated addresses with the responder addresses; and a switch to enable responses only when said demodulated addresses match said responder address; and a vehicle, said interrogation unit transported in said vehicle, such that said interrogation pulses and said responses are transmitted and received as said vehicle passes in proximity with the structure to be monitored.

12. The system of claim 11, wherein each of said corrosion sensors comprises:

a reference electrode; and a sensor electrode, such that corrosion affecting said metal in said structure also affects said sensor electrode so that the potential difference between said electrodes is indicative of corrosion.

13. The system of claim 12 wherein said electrode is made of the same metal as said metal reinforcement members.

14. The system of claim 11, wherein each of said responders further comprises read circuitry to generate data based on said output from an associated corrosion sensor.

15. The system of claim 14, wherein said read circuitry comprises:

a voltage follower coupled to said corrosion sensor;

an analog to digital converter coupled to said voltage follower;

a processor coupled to said analog to digital converter; and a memory coupled to said processor, such that said processor directs data from said analog to digital converter to said memory.

16. The system of claim 14, wherein said read circuitry comprises:

a voltage follower coupled to said corrosion sensor, said voltage follower generating a voltage based on said corrosion sensor output;

a comparator coupled to said voltage follower, said comparator having a first output state and a second output state, depending on the level of said corrosion sensor output;

a processor coupled to said comparator; and a memory coupled to said processor, said processor to store information related to the state of said comparator to said memory.

17. A method of sensing corrosion on a structure at least partially constructed with metal, comprising the steps of:

disposing corrosion sensors proximate said metal in said structure to be monitored:

transmitting interrogation pulses from an interrogation unit to a plurality of responders, each responder associated with one of said corrosion sensors;

receiving the interrogation pulses at the responders;

powering the responders from the interrogation pulses;

sensing corrosion with the corrosion sensors; and transmitting responses to the interrogation pulses based on information from the corrosion sensors.

18. The method of claim 17, wherein said step of sensing corrosion comprises sensing the potential difference between a reference electrode and a sensor electrode at the corrosion sensors.

19. The method of claim 17, and further comprising the step of driving a vehicle in proximity with the structure to be monitored, the interrogation unit being transported by the vehicle, the interrogation pulses being transmitted while the vehicle is in proximity with the structure.

20. The method of claim 17, and further comprising the steps of:

modulating at least some of the interrogation pulses to provide individual responder addressing;

at each responder, demodulating the interrogation pulses into addresses;

at each responder, comparing the demodulated addresses with a responder address; and at each responder, responding only when the demodulated addresses match the responder address.

21. The method of claim 17, wherein said step of transmitting interrogation pulses comprises transmitting wake-up pulses and address pulses, and, at each responder, further comprising the steps of:

storing energy from the wake-up pulses and the address pulses;

demodulating interrogation pulses into addresses;

comparing the demodulated addresses with a responder address; and responding only when the demodulated addresses match the responder address.

* * * * *